United States Patent [19]

Carter

[11] Patent Number: 5,091,374

[45] Date of Patent: * Feb. 25, 1992

[54] DOUBLE-STRANDED RNA CORRECTION OF ABNORMALITIES IN CIRCULATING IMMUNE COMPLEXES AND MONOCYTE FUNCTION

[75] Inventor: William A. Carter, Birchrunville, Pa.

[73] Assignee: HEM Research Inc., Rockville, Md.

[*] Notice: The portion of the term of this patent subsequent to Jan. 3, 2006 has been disclaimed.

[21] Appl. No.: 698,325

[22] Filed: May 6, 1991

Related U.S. Application Data

[63] Continuation of Ser. No. 490,503, Feb. 28, 1990, abandoned, which is a continuation of Ser. No. 252,003, Sep. 30, 1988, abandoned, which is a continuation of Ser. No. 124,577, Nov. 24, 1987, abandoned, which is a continuation-in-part of Ser. No. 74,616, Jul. 17, 1987, abandoned.

[51] Int. Cl.$^5$ .............................................. A61K 31/70
[52] U.S. Cl. ...................................... 514/44; 514/885; 536/27; 536/28; 536/29
[58] Field of Search .................. 514/44, 885; 536/27, 536/28, 29, 23

[56] References Cited

U.S. PATENT DOCUMENTS

| 3,796,631 | 3/1974 | Choay et al. | 514/44 |
|---|---|---|---|
| 4,020,696 | 4/1989 | Carter | 514/44 |
| 4,024,241 | 5/1977 | Levy | 536/28 |
| 4,130,641 | 12/1978 | Ts'o et al. | 514/44 |
| 4,313,938 | 2/1982 | Arimura et al. | 514/44 |
| 4,400,375 | 8/1983 | Douthart et al. | 536/29 |
| 4,795,744 | 1/1989 | Carter | 514/44 |
| 4,950,652 | 8/1990 | Carter | 514/44 |

FOREIGN PATENT DOCUMENTS

| 0113162 | 7/1984 | European Pat. Off. | 514/44 |
|---|---|---|---|
| 2503442 | 7/1975 | Fed. Rep. of Germany | 514/44 |
| 0042632 | 3/1982 | Japan | 514/44 |

OTHER PUBLICATIONS

Levy et al., Proceeding of National Academy of Science 62, No. 2 pp. 357–361 (1969).
Krown et al., The Chemical Abstracts 106: 154300s (1987).
Kleinerman et al., The Chemical Abstracts 105: 189137a (1986).
Zueva et al., The Chemical Abstracts 104: 18454b (1986).
Pahwa et al., The Chemical Abstracts 99: 36952v (1983).

Primary Examiner—John W. Rollins
Assistant Examiner—James O. Wilson
Attorney, Agent, or Firm—Nixon & Vanderhye

[57] ABSTRACT

Abnormalities in the circulating immune complexes in a patient's blood, such as observed in patients having inflammatory disorders, viral infections, or simply deranged immune function, are restored to normal or viral immunity conferred by the administration of a matched or mismatched dsRNA.

10 Claims, No Drawings

DOUBLE-STRANDED RNA CORRECTION OF ABNORMALITIES IN CIRCULATING IMMUNE COMPLEXES AND MONOCYTE FUNCTION

CROSS-REFERENCE TO RELATED APPLICATIONS

This is a continuation of application Ser. No. 07/490,503, filed Feb. 28, 1990, now abandoned which is a continuation of Ser. No. 07/252,003, filed Sept. 30, 1988, now abandoned which is a continuation of Ser. No. 07/124,577, filed Nov. 24, 1987, now abandoned which is a continuation-in-part of Ser. No. 07/074,616 filed July 17, 1987, now abandoned.

A variety of major inflammatory disorders of man are characterized by circulating immune complexes (CIC), which are principally antibody-antigen complexes in serum. Persistent CICs are etiologically associated with a number of diseases, including systemic lupus erythmatosis (SLE), rheumatoid arthritis (RA), various malignancies, AIDS, as well as infectious diseases due to other viruses, bacteria and parasites. The normal process of CIC clearance, i.e., removal by monocytes/macrophages, following their transport to the liver is also deranged in the above diseases plus other related disorders. Thus, associated disorders of peripheral blood monocyte functions and phagocytic capacity are commonly observed in these identical patient groups; collectively, these deficits may often lead to massive inflammatory destruction of various bodily tissues as well as decreased capacity to withstand various bacteria, viral and fungal pathogens to which these individuals are inevitably exposed.

I describe herein a novel method by which the majority of these functional defects can be controlled with a concurrent improvement in clinical status. Specifically, I describe a procedure, utilizing double-stranded RNAs, which simultaneously reduced CIC abnormal immune product depositions, and also improves monocyte function—all untoward effects to the human subject. Also described are procedures for protecting thymus and bone marrow derived cells from virus infection and/or spread in which the subject is given an effective quantity of a matched or mismatched dsRNA capable of conferring viral resistance without adverse cellular toxicity.

BACKGROUND OF THE INVENTION

Usually beginning as a benign process of a normally functioning immune system, immune complex formation may initiate injury to various organs and tissues. The activation of complement, a normal blood product, by CICs can lead to a series of destructive events, including cell lysis and deposition of CICs on various vessel walls, cell membranes, etc. The antigens responsible for initiating such a pathogenic immune response are often unknown in specific clinical practice, but may be microorganisms, tumors or, indeed, the body's own tissues. Infectious diseases such as hepatitis B can also be accompanied by immune complex disease. CICs are so far reaching in relationship to diagnosis and measuring the efficiency of therapy in various clinical situations such that, in the last 10 years, more than 40 assays have been developed to detect and quantify such immune complexes in human pathologic fluids. The brochures prepared by industry leaders (e.g., Maryland Medical Laboratory brochure, designated 4/87 or Roche Biomedical Laboratories brochure, prepared in 1987), attest to the magnitude of the chemical problems secondary to enhanced CIC production in man. Table 1 of the Maryland Medical Laboratory brochure is hereby incorporated by reference to indicate the range of the diseases associated with CICs.

CICs may actually contain virus particles as in the case of virus inclusion of the AIDS virus itself in CICs of AIDS patients (Morrow et al, *Clin. Immunology and Immuno Pathology*, Vol. 40, p. 515, 1986). The CICs, especially if present in high concentrations, may actually cause an immunosuppressive effect and can even cause blockade of the body's vital reticuloendothelial system (see references cited in Morrow et al). Thus, circulating ICs may be one of the reasons for the abnormal functioning of monocytes-macrophages in many human and animal diseases, including AIDS. Accordingly, it is clear that, while formation of "small" amounts of IC may be part of a normal pathophysiological response to disease, inappropriate synthesis of IC will cause and/or accelerate various diseases.

Immune complex formation is a useful parameter particularly in assessment of rheumatic diseases, such as rheumatoid arthritis and systemic lupus. Specifically, elevated levels of immune complexes seem to track disease activity in many patients over time.

Among the methods used to evaluate CICs in man is the assay for the CR1 receptor, a glycoprotein that binds certain fragments (notably C3G and C4G) of the complement system. Erythrocytes or red blood cells (RBCs) carry on their surface the majority of CR1 receptors in the body's circulation. CR1 appears to endow RBCs with the capacity to clear CICs by transporting them to the liver where they are removed by local monocytes/macrophages (see Tausk et al, *J. Clin. Investigation*. Vol. 78, p. 977, 1986, and articles cited therein). Various diseases involving autoantibodies and CIC, such as arthritis, leprosy and AIDS, are associated with low levels of erythrocyte CR1.

Two different designators for the AIDS virus exist; LAV is the designator for the AIDS virus isolated at the Pasteur Institute, Paris, France, and HTLV-III is the designator for the AIDS virus isolated at the National Institute of Health, Bethesda, Md., U.S.A. Frequently in this text, the AIDS virus will be referred to generically or designated HTLV-III or LAV without intending to differentiate between them. Furthermore, the term "AIDS virus" in the specification and claims includes any and all other viruses which may be associated with producing AIDS, whether yet isolated or not.

DESCRIPTION OF THE INVENTION

I evaluated a group of individuals with evidence of prior AIDS virus infection to determine the various relationships between CIC level, CR1 level and disease severity (clinical status). Additionally, I employed other tests (referred to as the direct Coombs test) to determine if immune complexes were bound to the subjects' RBCs and the extent to which their reticuloendothelial systems, as probed by monocyte function and number, were operational upon completion of these base line measurements. I discovered that I could indeed reverse both the immunological derangements and deteriorated clinical status in a coordinate manner by administration of certain dsRNA molecules. I considered AIDS as a prototypic immunological derangement with knowledge gained immediately applicable to a spectrum of other diseases.

I first selected individuals with a prior history of AIDS virus exposure because (a) they have emerged as the prototype group manifesting high immune complex levels (see McDougal et al, *J. Clin. Immun.*, Vol. 5, p. 130, 1985 and references cited therein), (b) the inciting (etiologic) microorganism is known, and (c) the disease is of unprecedented importance in the chronicles of public health. Finally, a variety of therapeutic modalities—drugs and biologics—(interferons, interleukins, thymus extracts, isoprinosine, thymus-derived polypeptide fractions, etc.) have been previously evaluated and none have shown any demonstrable ability to alter either the profound immune derangements, or the inexorable downhill clinical course. Finally, there are many compelling reasons that the identification of a novel therapeutic regimen, i.e., refraction of immune complex formation or increase in its clearance, would have profound ramifications in many other human disorders. Indeed, new evidence indicates that decremental loss of CR1 activity (due to progressive CIC formation) is associated with progression of retroviral/inflammatory diseases from an asymptomatic "carrier" state to a terminal moribund condition (see Inada et al, *AIDS Research*, Vol. 2, p. 235, 1986 and references cited therein).

By "matched dsRNA" are meant those in which hydrogen bonding (base stacking) between the counterpart strands is relatively intact, i.e., is interrupted on average less than one base pair in every 29 consecutive base residues. The term "mismatched dsRNA" should be understood accordingly.

The dsRNA may be a complex of a polyinosinate and a polycytidylate containing a proportion of uracil bases or guanidine bases, e.g., from 1 in 5 to 1 in 30 such bases (poly I. poly $(C_{4-29} \times > U$ or G).

The dsRNA may be of the general formula $rI_n \cdot r(C_{12}U)_n$. Other suitable examples of dsRNA are discussed below.

The mismatched dsRNAs preferred for use in the present invention are based on copolynucleotides selected from poly $(C_n,U)$ and poly $(C_n,G)$ in which n is an integer having a value of from 4 to 29 and are mismatched analogs of complexes of polyriboinosinic and polyribocytidilic acids, formed by modifying $rI_n \cdot rC_n$ to incorporate unpaired bases (uracil or guanine) along the polyribocytidylate $(rC_n)$ strand. Alternatively, the dsRNA may be derived from poly (I). poly (C) dsRNA by modifying the ribosyl backbone of polyriboinosinic acid $(rI_n)$, e.g., by including 2'-O-methyl ribosyl residues. These mismatched analogs of $rI_n \cdot rC_n$, preferred ones of which are of the general formula $rI_n \cdot r(C_{11-14},U)_n$ $rI_n lr(C_{29},G)_n$, are described by Carter and Ts'o in U.S. Pat. Nos. 4,130,641 and 4,024,222 the disclosures of which are hereby incorporated by reference. The dsRNA's described therein generally are suitable for use according to the present invention.

Other examples of mismatched dsRNA for use in the invention include:

poly (I). poly $(C_4, U)$
poly (I). poly $(C_7, U)$
poly (I). poly $(C_{13}, U)$
poly (I). poly $(C_{22}, U)$
poly (I). poly $(C_{20}, G)$
poly (I). poly $(C_{29}, G)$ and
poly (I). poly $(C_p)$ 23 G>p Also, as used in this application, the term lymphokines includes interferons, preferably interferon alpha, the interleukins, specifically interleukin-1 (IL-2) and recombinant interleukin-2 (rIL-2), and tumor necrosis factor (TNF). Also included are lymphokine activated killer cells (LAK) formed in animals in response to exposure to a lymphokine.

When interferon (alpha) is used as the lymphokine an amount of from 0.01 to 100,000 IRU per milliliter of the patient's body fluid is provided. When IL-2, preferably rIL-2, is the lymphokine, the amount administered lies within a range of about $10^2$ IL-2 units per kg of the patient's body weight up to a value approaching unacceptable levels of toxicity in that patient, which may be as high as $10^6$ IL-2 units. However, most effective, toxic-reaction manageable values are in the range of from about $10^3$ to about $10^4$ IL-2 units per kg of body weight.

The usual amounts of dsRNA administered provide a level of from 0.1 to 1,000 micrograms dsRNa per milliliter of the patient's body fluid. Body fluid is intended to refer to that solution of serum, salts, vitamins, etc., which circulates within the organism and bathes the tissues. When both agents are administered as previously described, the two active agents may be administered as a mixture, administered separately but simultaneously, or sequentially.

Administration of a dsRNA and a lymphokine "in combination" includes presentations in which both agents are administered together as a therapeutic mixture, and also procedures in which the two agents are administered separately but simultaneously, e.g., as through separate intravenous lines into the same individual. Administration "in combination" further includes the separate administration of one of the drugs in which one of the drugs is given first and followed shortly by the second.

Restoration of Altered Immune Complex Formation by dsRNAs: Table 1 shows representative clinical results before, during and after administration of a dsRNA, $rI_n Ir(C_{11-14}U)_n$, 50–200 mg given twice a week to approximately 60 kilogram individuals. The Immune Complex test (Inada, 1986, reference cited above) looked for immune complexes capable of implementing the entire compliment activating process. Briefly, heat-inactivated patient serum and guinea pig complement were first combined and then reduced (using dTT, dithiothreitol) and, finally, added to normal RBCs as indicator cells with a known, predetermined content of free CR1 receptors. If immune complexes were present in the patient's serum, the indicator RBCs will aggregate; this is referred to as immune adherence hemagglutination of IAHA. I used the "free" CR1 receptor test to determine the level of "free" CR1 receptor activity on the patient's RBCs, e.g., compare the results in my Table 1 with those of Inada in various untreated individuals (as shown in his FIG. 1, *AIDS Research*. Vol. 2, No. 3, p. 238, 1986)). I first mixed immune complexes, complement and the patient's RBC "ghosts", a technique described by Inada and well known to those in the art. If the patient's RBCs have available CR1 receptor, the CICs are bound such that when indicator RBCs (from normals) are added, no CICs are in free solution and the indicator RBCs do not aggregate. If degrees of aggregation do occur, it indicates that the patient's RBC ghosts were not able to bind CICs due to the absence of available CR1 receptors. The absence of CR1 receptors in this case appears to be due to the saturation of such receptors by the high (abnormal) level of circulating immune complexes. Low levels of "free" CR1 receptor is a bad prognostic sign and often correlates with a high level of CICs.

TABLE 1

Relationships Between CIC Levels, "Free" CR1 Receptor Content Direct Coombs' Test and the Effectiveness of dsRNA Administration on Correcting These Abnormal (Pathogenic) Immunologic Parameters

| Patient | Hematocrit | Immune Complex micrograms/ml | "free" CR1 Receptor | Direct Coombs' Test |
|---|---|---|---|---|
| 1. Rejo, pretreat. | 40 | 32 | — | IgG, IgM, $C_3$ |
| 2 weeks | 40 | 16 | + | IgG, IgM, $C_3$ |
| 4 weeks | 36 | 4 | ++ | IgG, IgM, $C_3$ |
| 8 weeks | 40 | 0 | +++ | IgG, IgM |
| 16 weeks | 40 | 0 | +++ | trace IgG |
| 2. Clin, pretreat. | 45 | 40 | — | IgM, $C_3$ |
| 2 weeks | 46 | 20 | + | O |
| 4 weeks | 45 | 0 | ++ | O |
| 8 weeks | 45 | 0 | ++ | O |
| 16 weeks | 45 | 0 | +++ | O |
| 3. Tuja, pretreat. | 36 | 36 | + | IgG, IgM, $C_3$ |
| 4 weeks | 34 | 28 | ++ | IgG, $C_3$ |
| 8 weeks | 35 | 16 | +++ | IgG, trace $C_3$ |
| 20 weeks | 35 | 4 | +++ | O |
| 40 weeks | 35 | 0 | ++++ | O |
| 4. Poca, pretreat. | 34 | 32 | — | IgG, IgM, $C_3$ |
| 8 weeks | 36 | 4 | + | IgG |
| 20 weeks | 36 | 4 | ++ | trace IgM, trace $C_3$ |
| 40 weeks | 36 | 0 | +++ | O |

Normal Volunteers (10) tested neg. for immuno complex, ++++ for CR1 and neg. for Coombs One can readily determine that I was able to restore these parameters of inflammatory disease to essential normalcy by dsRNA administration. A comparison of Table 1 from the evidence given in the immediately preceding Table above, with FIG. 1 and Table 1 of Inada et al clearly shows that my results with diseased patients, after dsRNA administration, very closely resembled the completely normal values of 37 healthy subjects reported by Inada et al with the same comprehensive laboratory parameters.

I have described above an overview of the Inada et al technique for "free" CR1 receptor which was used in the context of this invention. I also utilized the technique of Inada et al to measure actual types of immune molecules bound to the patient's RBCs (the direct Coombs' test) before, during and after dsRNA administration. Specifically, two classes of immunoglobulius—designated IgG and IgM—when bound to RBCs are indicative of an active, abnormal immune process. For example, Inada found no normal subjects with a positive direct Coombs' test, whereas 64–84% of patients with active retroviral infection were readily positive an degree of positivity correlated with clinical status. Also, I measured whether or not these RBCs were coated with a specific component of the complement system, designated $C_3$, which is also an additional reliable marker of an abnormal immune or inflammatory reaction. Specifically, the presence of $C_3$ on RBCs indicates an activation of the complement system or cascade in which $C_1$, $C_4$, $C_2$ and finally $C_3$ are sequentially bound to RBCs. Again, I demonstrated over time the completely unexpected finding that dsRNA could correct the abnormal concentration of inflammatory system components (e.g., IgG, IgM and $C_3$ molecules) from attaching to the patient's circulating RBCs.

Importantly, the kinetics of recovery of different limbs of the immune response in my work also showed that I was addressing with dsRNA an apparent root cause of the fundamental disease process. For example, immune complex level fell quickly (Table 1), correlating with the rapid clinical improvement whereas the direct Coombs' test improved more slowly. My observations support the thesis that (a) "wash out" of the abnormal Coombs' test is slow and often requires 2-3 months—the approximate life span of the erythrocyte—to clear, whereas (b) CIC levels fall more quickly because their appearance initially is usually only after saturation of the RBCs with abnormal immune complexes as measured by the direct Coombs' test. A comparison of my Table 1 (last column, direct Coombs' data) with FIGS. 2 and 3 of Inada presents compelling evidence of the effect that I was indeed able to correct those profound immunologic derangements in my patient group to the essential normalcy as defined by immunological criteria developed completely independently by Inada et al with a completely healthy and normal population group, e.g., note that in Inada's group, no healthy subject had detectable immunoglobulin determinants or complement $C_3$ fragments on their RBCs.

Restoration of Altered Function of Blood Monocytes: Even though the functions of monocyte-macrophages play a central role in (a) initiation and modulation of immune response as well as in (b) defense mechanisms against microorganisms these cells have been the subject of very few studies; see Roux-Lombard et al, *European J. of Clin. Investigation*, Vol. 16, p. 262, 1986 and references cited therein. For example, monocytes/macrophages can phagocytose (engulf) various microorganisms and produce reactive oxygen intermediates with high bactericidal potency. They also can secrete protaglandins which are known to alter T-cell functions. Thus, in view of their complementary and pivotal role in immune modulation vis a vis the other parameters I examined in Table 1, I studied both monocyte phagocytic and bactericidal capacity (a critical function) and number of peripheral cells before, during and after dsRNA administration in an identical group of individuals.

Mononuclear cells were obtained by me from heparinized blood by density gradient centrifugation in Ficoll-Hypaque. Their viability, as assessed by the trypan blue dye exclusion test, was greater than 95%. I then measured monocyte as well as T-lymphocyte subpopulations by use of standard monoclonal antibodies, including $MO_2$ (for monocytes), $OKT_3$, $OKT_4$, $OKT_8$, etc., followed by fluorescein-conjugated goat anti-mouse immunoglobulins obtained from Ortho Diagnostics, Inc., Raritan, N.J., U.S.A., to facilitate their enumeration.

TABLE 2

Restoration of Diminished Function/Number of Blood Monocytes in Individuals with Circulating Circulating Immune Complexes by dsRNA Administration

| Patient | % Monocytes (MO2 Marker) | Number Monocytes (per cuomilliliter) | % Killed Bacteria (normal range = 10–62%) |
|---|---|---|---|
| 1. Rajo, pretreat | 1 | 55 | 0 |
| 2 weeks | 6 | 330 | 4 |
| 4 weeks | 12 | 660 | 10 |
| 8 weeks | 18 | 990 | 18 |
| 16 weeks | 17 | 935 | |
| 2. Clin, pretreat | 2 | 126 | 3 |
| 2 weeks | 8 | 504 | 10 |
| 4 weeks | 13 | 819 | 35 |
| 8 weeks | 15 | 945 | 40 |
| 16 weeks | 19 | 1197 | 40 |
| 3. Tuja, pretreat | 2 | 98 | 0 |
| 4 weeks | 11 | 539 | 4 |
| 8 weeks | 10 | 490 | 15 |
| 20 weeks | 12 | 588 | 20 |
| 40 weeks | 18 | 882 | 35 |
| 4. Poca, pretreat | 1 | 40 | 2 |
| 8 weeks | 9 | 315 | 16 |
| 20 weeks | 12 | 420 | 24 |
| 40 weeks | 20 | 700 | 40 |

I also evaluated bactericidal capacity by the standard technique using *Staphylococcus aureus* in the presence of either autologous or pooled type AB serum (Cruchard et al, *Diagnostic Immunol.*, Vol. 2, p. 203, 1984, the disclosure of which is hereby incorporated by reference). In Table 2, I express results as the percentage of bacteria that were killed after a 1 hour incubation.

Table 2 shows that there is indeed an unexpected and rapid recovery of both monocyte number and functions in the immunocompromised humans who received the scheduled administration of the mismatched dsRNA designated $rI_n \cdot r(C_{11-14}, U)_n$, also called Ampligen ™. Previous attempts by others to restore such function by use of other lymphokines have unfortunately resulted in failure. When Tables 1 and 2 are compared, it is apparent that I have accomplished a multifaceted effect in terms of restoring multiple limbs of the immunological capacity simultaneously, and I have accomplished this effect with favorable kinetics of response and apparent lack of host toxicity.

Table 3 shows that the protective effect of dsRNA extends well outside the various T cells components of the immune system. Here data are introduced to indicate effectiveness of dsRNA in protecting cells of bone marrow lineage such as, but not limited to, monocytes/macrophages. T cells are considered to have a thymus-derived lineage, hence I demonstrate here the additional capacity of certain dosages of dsRNAs to protect specifically human cells of both bone marrow and thymus derived origin; that is, the cells can be protected from animal viral infection without a detectable adverse effect on normal cellular functions including their replicative cycles. An HIV (virus) is used as a prototype because it is capable of mimicking other viruses either with acute cytolytic potential, subacute cytolytic potential, or even genomic integrative potential (latency and/or cancer-provoking potential).

Table 3 confirms the antiviral effect on various viral isolates (e.g., HTLV-III$_B$ and HTLV III$_{RF}$) as well as various target cells (e.g., U937 or H9 cells).

Preventing and/or controlling infection in bone marrow derived cells without toxicity is highly relevant therapeutically since many animal viruses in fact use such cells as a primary or secondary viral source reservoir. For example, HIV may use macrophages, megakaryocytes and various cells which respond to colony stimulating factors as a significant aspect of its pathogenesis and ability to escape from the host's immunosurveillant capacities.

TABLE 3

AMPLIGEN EFFECT IN VITRO ON AN HIV PERMISSIVE HUMAN MONOCYTE/MACROPHAGE CELL LINE (U327)

| Culture Conditions[a] | DAY | | | | | | | |
|---|---|---|---|---|---|---|---|---|
| | 2 | 4 | 6 | 8 | 10 | 12 | 14 | |
| U937/HTLV-III$_B$ | — | — | $9.6 \times 10^4$ | $2.0 \times 10^6$ | $1.6 \times 10^7$ | $5.1 \times 10^6$ | — | RT Activity (cpm/ml)[b] |
| No Ampligen | — | 3–5 | 15–18 | 40 | 100 | 100 | — | % IIF[c] |
| U937/HTLV-III$_B$ | — | — | $8.0 \times 10^3$ | $3.0 \times 10^4$ | $1.6 \times 10^5$ | $1.0 \times 10^6$ | — | RT Activity (cpm/ml) |
| Ampligen (50 μg/ml) | — | <1 | 1 | 2–3 | 5 | 30 | — | % IIF |
| H9/HTLV-III$_{RF}$ | — | — | $3.8 \times 10^4$ | $1.6 \times 10^6$ | $1.8 \times 10^7$ | $9.6 \times 10^6$ | — | RT Activity (cpm/ml) |
| No Ampligen | — | 1–2 | 5 | 20–25 | 100 | 100 | — | % IIF |
| H9/HTLV-III$_{RF}$ | — | — | 0 | 0 | $2.4 \times 10^4$ | $2.4 \times 10^5$ | — | RT Activity (cpm/ml) |
| Ampligen (50 μg/ml) | — | <1 | <1 | <1 | 2–4 | 5–7 | — | % IIF |
| H9/HTLV-III$_B$ | — | — | 0 | $3.0 \times 10^4$ | $8.6 \times 10^5$ | $7.2 \times 10^6$ | — | RT Activity (cpm/ml) |
| No Ampligen | — | 1 | 1–2 | 5–7 | 20–30 | 100 | — | % IIF |
| H9/HTLV-III$_B$ | — | — | 0 | 0 | 0 | $5.6 \times 10^4$ | — | RT Activity (cpm/ml) |

TABLE 3-continued

AMPLIGEN EFFECT IN VITRO ON AN HIV PERMISSIVE HUMAN MONOCYTE/MACROPHAGE CELL LINE (U327)

| Culture Conditions[a] | DAY | | | | | | | |
|---|---|---|---|---|---|---|---|---|
| | 2 | 4 | 6 | 8 | 10 | 12 | 14 | |
| Ampligen (50 μg/ml) | — | <<1 | <<1 | <1 | 1 | 5-7 | — | % IIF |

[a]Producer cell/HIV-1 isolate using U937 cells as targets with or without Ampligen as indicated.
[b]RT = Reverse transcriptase
[c]IIF = Indirect immunofluorescence expressed as % positive cells using a human anti-p24 serum.

What is claimed is:

1. A method of restoring the immunological capacity of macrophages and monocytes exposed to human immunodeficiency virus in a patient infected with human immunodeficiency virus, comprising administering to said patient an effective amount of a mismatched dsRNA that is (1) a complex of a polyinosinate and a polycytidylate containing from 1 to 5 to 1 to 30 uracil or guanidine unpaired bases or (2) a copolynucleotide having the formula poly($C_n$,U) or poly($C_n$,G) in which n is an integer having a value of from 4 to 29 and are formed by modifying poly($I_n$)·poly($C_n$) to incorporate the unpaired base uracil or guanidine along the poly ($C_n$) strand.

2. The method of claim 1 in which the mismatched dsRNA is a poly I complexed with poly C.

3. The method of claim 2 in which the poly I complexed with poly C is additionally complexed with a RNA-stabilizing polymer.

4. The method of claim 3 in which the stabilizing polymer is lysine or cellulose.

5. The method of claim 1 in which the dsRNA is polyadenylic acid complexed with polyuridylic acid.

6. The method of claim 2 in which a mismatched dsRNA is administered.

7. The method of claim 6 in which the mismatched dsRNA is a complex of a polyinosinate and a polycytidylate containing from 1 in 5 to 1 in 30 uracil or guanidine bases.

8. The method of claim 7 in which the mismatched dsRNA is $rI_n \cdot r(C_{11-14},U)_n$.

9. The method of claim 1 which the dsRNA contains regions of bond breakage and the dsRNA exhibits the favorable therapeutic ratio property of $rI_n \cdot r(C_{11-14},U)_n$.

10. The method of claim 6 in which the mismatched dsRNA is administered in an amount which will result in a level of from 1 to 1,000 micrograms per milliliter of the patient's body fluid.

* * * * *